US00PP17768P3

(12) United States Plant Patent
Orton et al.

(10) Patent No.: US PP17,768 P3
(45) Date of Patent: May 29, 2007

(54) INTERSPECIFIC HYBRID DOGWOOD TREE DESIGNATED 'KF1-1'

(50) Latin Name: ***Cornus kousa*×*C. florida***
Varietal Denomination: KF1-1

(75) Inventors: Elwin R. Orton, Hillsborough, NJ (US); David A. Gant, Wall Township, NJ (US)

(73) Assignee: Rutgers, The State Universtiy, New Brunswick, NJ (US)

( * ) Notice: Subject to any disclaimer, the term of this patent is extended or adjusted under 35 U.S.C. 154(b) by 0 days.

(21) Appl. No.: 11/194,349

(22) Filed: Aug. 1, 2005

(65) Prior Publication Data

US 2007/0028335 P1 Feb. 1, 2007

(51) Int. Cl.
*A01H 5/00* (2006.01)

(52) U.S. Cl. ..... Plt./220

(58) Field of Classification Search ..... Plt./220
See application file for complete search history.

*Primary Examiner*—Kent Bell
*Assistant Examiner*—June Hwu
(74) *Attorney, Agent, or Firm*—James A. Lucas; Driggs, Hogg & Fry Co., L.P.A.

(57) ABSTRACT

An $F_1$ interspecific hybrid of *Cornus kousa*×*C. florida* that is distinguished by its large bracts, a compact and dense attitude, wider than tall, and a flowering habit in the middle of the blooming season for the commercially available cultivars of *Cornus kousa*×*C. florida*. The cultivar has a high level of winter hardiness, and is highly resistant to dogwood anthracnose and the common dogwood borer.

2 Drawing Sheets

Botanical designation: $F_1$ interspecific hybrid of *Cornus kousa*×*C. florida*.
Variety denomination: 'KF1-1'.

BACKGROUND OF THE INVENTION

This new cultivar is the product of a long standing detailed program of interspecific hybridization and selection of dogwoods, in this instance a controlled cross of an $F_1$ interspecific hybrid of a *Cornus kousa*×*C. florida*. The purpose of the program was to develop new and superior cultivars of large-bracted dogwoods. The seed parent of this new cultivar is an unnamed seedling of unknown origin of *Cornus kousa* and the pollen parent is an unnamed seedling of unknown origin of *Cornus florida*. The progeny were carefully retained and characteristics analyzed for their differences and outstanding value as potential commercial varieties or cultivars.

We have selected the particular seedling hereof from certain progeny grown in a cultivated area and, as a result, have in turn caused the same to be asexually reproduced by grafting. The reproduction and actual growth and selection of the new cultivar took place in the vicinity of New Brunswick, N.J. The claimed cultivar is stable and reproducible true to type in successive generations of asexual reproduction.

As will be understood from the detailed description of the invention which appears hereinafter, the new cultivar is in fact outstanding and readily identified as being such. With the foregoing in mind, the description which follows will be understood as clearly defining the new cultivar, the desirable characteristics of which are the result of such a program as has been heretofore suggested.

SUMMARY OF THE INVENTION

The variety was originated in a cultivated field at New Brunswick, Middlesex County, N.J. 08901. This seedling resulted from a controlled cross made in June of 1968.

The seedling which became this new variety germinated in February of 1969, was transplanted to progressively larger containers, was transplanted to the field in June 1972 at said horticulture farm in North Brunswick, N.J. Two cuttings were taken from this original seedling in August of 1971, were successfully rooted and were subsequently field planted at the horticulture farm in June of 1973 for further observation along with the original seedling.

The dogwood tree of the present invention is asexually propagated by grafting (usually T-budding or chip-budding) or by softwood cuttings. It is distinguished from the other 6 patented commercially available cultivars of *Cornus kousa*× *C. florida* in the following respects:

Aurora® U.S. Plant Pat. No. 7,205 'Rutban' has bracts that are rounded, heavily overlapping, and velvety textured whereas the bracts of 'KF1-1' are not. Aurora® typically blooms about 2 days after 'KF1-1'.

'KF1-1' is more compact and dense than Celestial® U.S. Plant Pat. No. 7,204 'Rutdan' and is wider than tall whereas Celestial® is taller than wide. 'KF1-1' blooms a day or two after Celestial®.

Constellation® U.S. Plant Pat. No. 7,210 'Rutcan'; Stardust® U.S. Plant Pat. No. 7,206 'Rutfan'; and Ruth Ellen® U.S. Plant Pat. No. 7,732 'Rutlan' all have flower heads with floral bracts that are distinctly separate with no overlap of adjacent floral bracts. They also flower earlier in the season than 'KF1-1'. Further Constellation® is more vigorous and become much larger than 'KF1-1'. Stardust® and Ruth Ellen® grow very low to the ground as a dense hedge with Stardust® being much smaller than and not as wide as Ruth Ellen®.

Stellar Pink® U.S. Plant Pat. No. 7,207 'Rutgan' has pink rather than white floral bracts. It blooms after 'KF1-1'.

BRIEF DESCRIPTION OF THE DRAWINGS

This new cultivar of dogwood is illustrated by the accompanying digitized photographic drawings, depicting the plant by the best possible color representation using color photography. All color references below are measured against The Royal Horticultural Society (R.H.S.) Colour Chart. Colors are approximate as color depends on horticultural practices, such as light level and fertilization rate, among others.

BOTANICAL DESCRIPTION OF THE INVENTION

Figure 1:
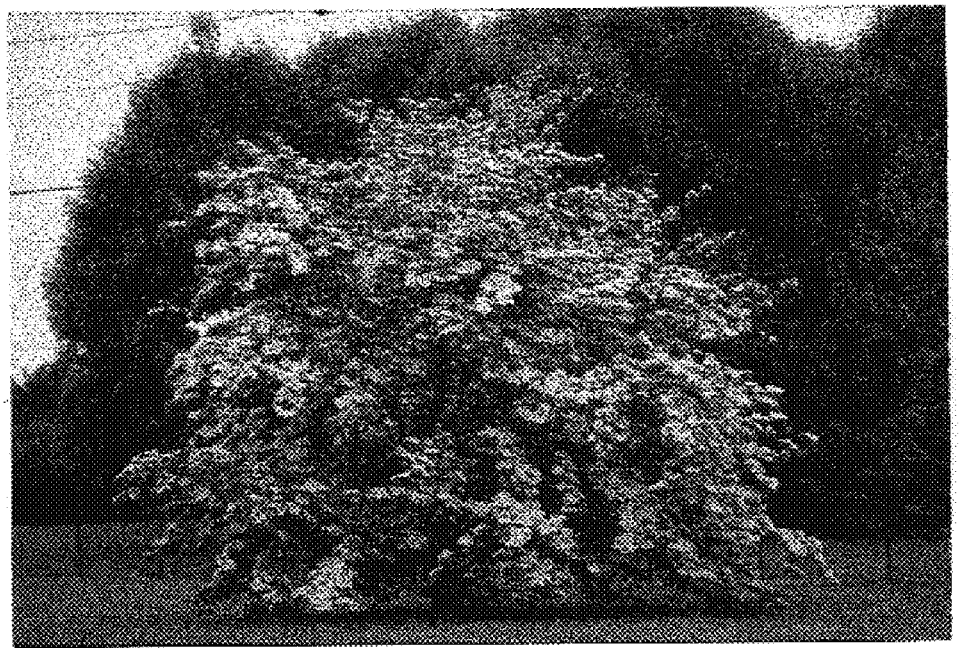
FIG. 1 shows a dogwood tree of the present invention after 29 growing seasons.
Figure 2:
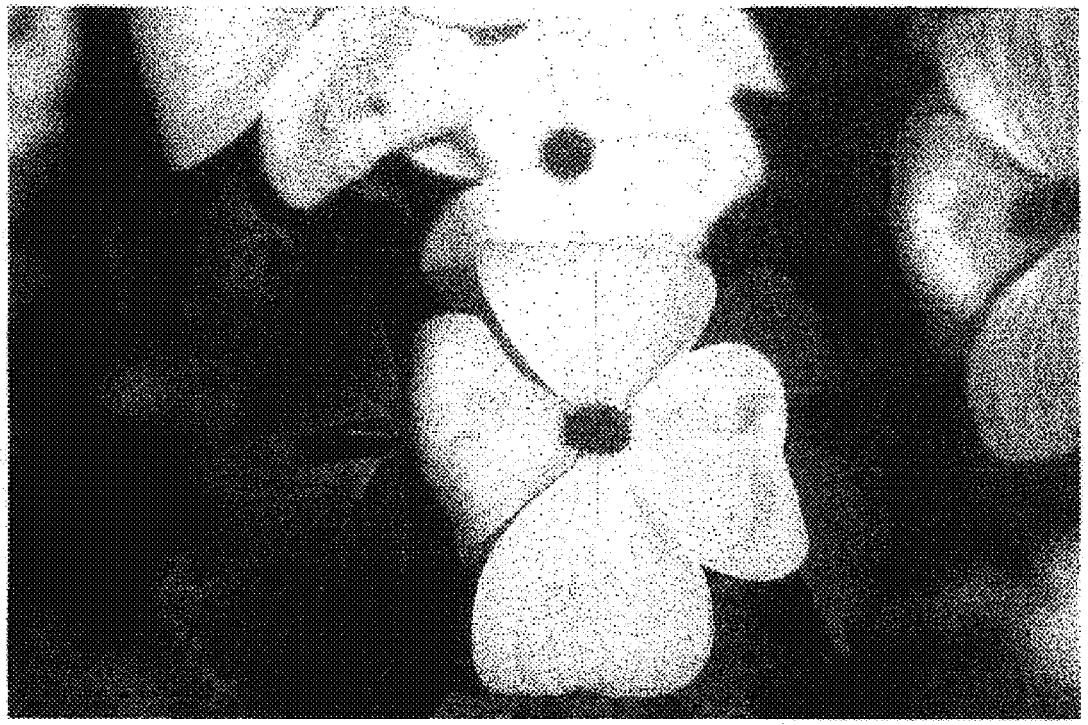
FIG. 2 shows several flower heads of the tree shown in FIG. 1 taken at the time of floral display, and indicates the color and shape of the floral bracts.

Form: Tree.

Growth habit: Dense tree branched low to ground with upright branches which form a rounded, but spreading, head. Very vigorous, but compact, and wider than tall.

*Height.*—6.7 meters at 36 years.

*Spread.*—7.84 meters at 36 years.

Plant vigor: Plants of this new variety are more vigorous than plants of current varieties of *C. kousa* or *C. florida.*

Cold hardiness: The original seedling, and two cutting-grown propagules thereof, have suffered no winter injury during the 33 and 31 winters since 1971 and 1973, respectively, that the plant cuttings have been under test in the field at New Brunswick, N.J. in USDA Plant Hardiness Map Zone 6a (−5° to −10° F.).

Resistance to insects and diseases: No evidence of insect or disease problems have been observed on the original seedling, or its propagules, in the many years the plants have been under test in New Jersey, and Tennessee. No powdery mildew observed on the plants grown in New Jersey and Tennessee, but some powdery mildew was observed on plants of 'KF1-1' under test in Oregon. No evidence of susceptibility to Dogwood anthracnose or common dogwood borer.

Trunk: Circumference of the trunk at 10 cms. above the soil level was 1.24 m after 36 growing seasons.

*Texture.*—Smooth when young, but becoming shaggy with age as then exhibits heavily exfoliating bark.

*Color of exfoliating bark.*—A mottled pattern of areas closest to 197A and 197B Greyed-Green Group and areas closest to 199B and 199D Greyed-Brown Group.

Color of smooth trunk under exfoliated bark is closest to 165C Greyed-Orange Group.

*Lenticels.*—Imperceptible on exfoliating bark. Three year branches sandpaper rough due to high number (average 69 — range 56–88 per $cm^2$). Size of lenticels 0.5–0.7 mm long by 0.3 mm–0.4 mm wide.

Branches:

*Color.*—Closest to 197A Greyed-Green Group.

*Texture.*—Smooth on young branches but becoming sandpaper rough with age.

*Crotch angle.*—35–55° for large, major branches but 45–70° for subsequent smaller branches.

FOLIAGE

Leaf arrangement: Opposite.

Leaf size: Blade. Average length 13.6 cm (range 11.8–16.8). Average width 6.9 cm (range 5.9–8.3), the widest point being a little more than half-way down from the tip.

*Shape.*—Ovate/elliptic.

*Tip.*—Apiculate.

*Base.*—Attenuate.

*No. of pairs of veins.*—Principally 5.

*Margin.*—Moderately wavy.

*Texture.*—Adaxial is quite smooth, although it has many minute whitish hairs. The abaxial surface is slightly fuzzy due to many minute, whitish hairs on the blade and tufts of longer, thin hairs along the midrib and the side veins.

*Quantity.*—Many, densely foliaged.

Coloration: Solid.

*Mature leaf color.*—Adaxial: Closest to 139A, Green Group, but Greener. Abaxial: 139C, Green Group.

*Petiole.*—Closest to 144B Yellow-Green Group.

*Immature leaf color.*—Adaxial: Closest to but darker than 144A Yellow-Green Group. Abaxial: Color in between 138B and 138C Green Group.

*Petiole.*—Closest to 146C Yellow-Green Group Autumn foliage color (mid-October), New Brunswick, N.J.

*Adaxial surface.*—Approximately 85 percent of leaves 137A Green Group with the other leaves predominantly green but mottled with other colors: mostly 187A Greyed-Purple Groups, 183A Greyed-Purple Group, 53A Red Group, 46A Red Group, 43A Red Group, and 9A Yellow Group. The color of the midrib from the petiole to the base of the uppermost pair of side veins shows a little yellow streak closest to 145C Yellow-Green Group.

*Abaxial surface.*—136D Green Group.

Leaf color is clearly dependent on many environment factors such as soil type, available water and nutrients, exposure to sun, air temperature and day length. Thus, autumn foliage color may vary from one area to another and from year to year. Some years, fall coloration is predominantly 187A and 187B Greyed-Purple Group.

*Petiole.*—Color at New Brunswick, N.J.

*May.*—Closest to 146C Yellow-Green Group.

*October.*—145A Yellow-Green Group.

INFLORESCENCE

Location where observations were made: New Brunswick, N.J.

Type of inflorescence: Flower head. Dense, rounded mound.

Peduncle size (in mid-June at time of flowering (n=20 measurements):

*Average length.*—3.84 cm (range=2.8 cm–5.0 cm).

*Average width.*—1.85 mm (range=1.5 cm–2.0 cm).

At the time of flowering, the peduncle length of the *C. kousa* parent averages about 7.3 cm and those of the *C. florida* parent average about 2.0 cm. Absolute peduncle length will vary slightly from year to year but the relative peduncle length among the hybrid 'KF1-1' and the two parents should remain consistent.

FLORAL BRACTS

Number: Four (two opposing pairs).

Size of floral bracts at time of floral period; mid-June.

TABLE 1

| | n | Average length | Average width |
|---|---|---|---|
| Inner, floral bracts | 50 | 5.36 cm | 4.25 cm |
| | 25 | Involucral spread: 10.91 cm | |

TABLE 2

| | n | Average length | Average width |
|---|---|---|---|
| Outer floral bracts | 50 | 4.58 cm | 4.67 |
| | 25 | Involucral spread: 9.35 cm | |

Where n=number of measurements.

The average length of the inner bracts is longer than the average length of the outer bracts. The average width of the inner bracts is less than the average width of the outer bracts. Bract length and width will vary slightly from year to year but the inner bracts will be longer and narrower than the outer bracts each year. This is consistent with the relative length and width of the inner and outer bracts of all of the other patented $F_1$ interspecific hybrids of *C. kousa*×*C. florida* in the trade today.

Shape: The floral bracts are basically obovate with a broad acuminate tip and a truncate end with a small, abruptly acute tip at the center. Similar to the floral bracts of Celestial® but distinctly different from those of the other five interspecific hybrids noted above.

Color: At peak of floral display: (approximately May 19):

*Adaxial.*—Closest to and in between 4C and 4D Yellow Group.

*Abaxial.*—Closest to 4D Yellow Group. Approximately May 27.

*Adaxial.*—Closest to 4D Yellow Group but much whiter.

*Abaxial.*—Closest to 155D White Group.

Flower description: Very floriferous. Single flowers arranged in compact, dense heads. (convex mound on flat base, 6.36 mm high and 9.38 mm wide). No observed fragrance. Flowers not persistent. Floral display of the involucral bracts last about 14–19 days, depending on weather conditions.

Flowering habit: Anthesis of the tiny, relatively inconspicuous true flowers generally begins a few days after onset of the ornamental display of the large floral bracts. The period of floral display (floral bracts) is intermediate to that of plants of the parent species: i.e., occurs in early to mid-May, commencing about two to four days after completion of the floral display of most plants of *C. florida* and ending about the time the floral display of early flowering plants of *C. kousa* begins.

Number of true flowers per flower head: The average number of true flowers per flower head in the hybrid 'KF1-1' is 36.3, (based on n=30 measurements), and is intermediate to that for the *C. kousa* parent (average=49) and that for the *C. florida* parent (34.5).

REPRODUCTIVE ORGANS

Stamens: Number per flower: 4.

*Filament.*—Length — approximately 2.75 mm (n=4). Width — approximately 0.28 mm (n=4). Color — 155B White Group.

*Anther.*—Length — approximately 0.4 mm (n=4). Width — approximately 0.81 mm (n=4). Color — 162A Greyed-Yellow Group.

*Pollen.*—Somewhat brownish-yellow.

Pistil:

*Style.*—Height — approximately 1.94 mm (n=4). Width — approximately 0.3 mm (n=4). Color — 144B Yellow-Green Group.

*Stigma.*—Height — approximately 0.25 mm (n=4). Width — approximately 0.5 mm (n=4). Color — 162A Greyed-Yellow Group. All figures are based on an average of the 4 measurements.

FRUIT

No fruit develops as the plants are sterile. The vast majority of flower heads drop after flowering.

What is claimed is:

1. A new and distinct cultivar of dogwood tree comprising an $F_1$ interspecific hybrid of *Cornus kousa*×*C. florida* substantially as herein shown and described.

* * * * *